US012576252B2

(12) United States Patent
    Brockmann et al.

(10) Patent No.: US 12,576,252 B2
(45) Date of Patent: Mar. 17, 2026

(54) IMPLANT

(71) Applicant: OLYMPUS WINTER & IBE GMBH, Hamburg (DE)

(72) Inventors: Christian Brockmann, Hollenstedt (DE); Martin Horn, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 289 days.

(21) Appl. No.: 18/142,660

(22) Filed: May 3, 2023

(65) Prior Publication Data

US 2024/0108868 A1 Apr. 4, 2024

Related U.S. Application Data

(60) Provisional application No. 63/411,241, filed on Sep. 29, 2022.

(51) Int. Cl.
    *A61M 29/00* (2006.01)
    *A61F 2/966* (2013.01)
    *A61F 2/04* (2013.01)

(52) U.S. Cl.
    CPC ............. *A61M 29/00* (2013.01); *A61F 2/966* (2013.01); *A61F 2002/047* (2013.01); *A61F 2250/001* (2013.01)

(58) Field of Classification Search
    CPC ..... A61M 29/00; A61M 27/008; A61F 2/966; A61F 2002/047; A61F 2250/001; A61F 2250/0004; A61F 2250/0007; A61F 2250/0059; A61B 17/00234; A61B 2017/00274; A61B 2017/00805; A61B 2017/32096
    See application file for complete search history.

(56) References Cited

U.S. PATENT DOCUMENTS

| | | | |
|---|---|---|---|
| 6,443,966 B1* | 9/2002 | Shiu ............... | A61B 17/320758 |
| | | | 606/159 |
| 2001/0047184 A1* | 11/2001 | Connors, III .......... | A61B 17/22 |
| | | | 604/101.04 |
| 2002/0077651 A1* | 6/2002 | Holmes, Jr. ........... | A61M 29/02 |
| | | | 606/190 |
| 2003/0060844 A1 | 3/2003 | Borillo et al. | |
| 2011/0028784 A1* | 2/2011 | Patil ................... | A61B 17/3423 |
| | | | 600/106 |
| 2011/0118735 A1* | 5/2011 | Abou-Marie ...... | A61B 18/1492 |
| | | | 606/45 |
| 2014/0142368 A1 | 5/2014 | Arnal et al. | |
| 2016/0101262 A1* | 4/2016 | Root ................... | A61M 25/005 |
| | | | 604/510 |

(Continued)

FOREIGN PATENT DOCUMENTS

| | | |
|---|---|---|
| CN | 113855320 A | 12/2021 |
| CN | 114145882 A | 3/2022 |

(Continued)

*Primary Examiner* — Richard G Louis
(74) *Attorney, Agent, or Firm* — Oliff PLC

(57) ABSTRACT

An implant with which prostates of different sizes can be treated is achieved by the fact that the length of a deployed implant is modifiable to a variable extent. Through the change of length of a stretched-out wire structure of the implant, the implant can be adapted individually to the patient anatomy and the outcome of treatment can thus be improved.

14 Claims, 2 Drawing Sheets

(56)  References Cited

U.S. PATENT DOCUMENTS

2018/0028222  A1    2/2018  Kilemnik
2018/0318114  A1    11/2018  Huang et al.

FOREIGN PATENT DOCUMENTS

DE      10 2004 062 444  A1     7/2006
DE      10 2019 115 021  A1    12/2020
DE      10 2021 133 207  A1     6/2023
WO         2008/136005  A2    11/2008
WO         2010/073244  A2     7/2010
WO         2015/101975  A1     7/2015
WO         2021/180044  A1     9/2021

* cited by examiner

IMPLANT

The invention relates to an implant according to the preambles of claims 1, 11 and 14.

Various methods and techniques are known for treating the urinary tract, in particular for treating benign prostatic hyperplasia (BPH). In a minimally invasive and particularly gentle treatment of BPH symptoms, a removable implant is temporarily placed in the urethra or in the prostatic portion of the urethra of the patient. Such an implant is a wire structure made of a shape-memory alloy, for example Nitinol. In a folded state, the wire structure is inserted through a catheter into the urinary tract and pushed to the correct position in order to deploy there into its predetermined basic structure. A tongue-like holding element, which can likewise be part of the implant, engages in the bladder neck in order to fix the wire structure. The wire structure, which can be formed from three or four wires, is a basket structure. This basket structure widens the urethra. Owing to the expansion of the wire structure against the tissue of the urethra, the tissue of the urethra becomes denatured over the course of a few days. This denaturation of the tissue takes place on account of the ischemic pressure of the individual wires on the cells of the tissue, which leads to reduced or completely absent blood flow. As a result, the lack of blood flow leads to a lack of oxygen in the cells and ultimately to the death of the cells. Within a few days, the tissue can be reduced to such an extent that the urinary flow almost normalizes. After completion of this treatment, the implant can be recovered from the urethra by means of a catheter.

For therapy also of the bladder neck during the treatment, the wires of the implant protrude into the bladder. The tongue-like holding element of the implant is pulled in order to lock the implant inside the prostate behind the bladder neck. The fact is, however, that the anatomies of patients are different, and the prostates may also have become enlarged to different extents. If the prostate is relatively short, there is a danger of the implant or the wires being placed too deep inside the bladder neck in the direction of the external sphincter. This can lead to the patient suffering temporary or even permanent incontinence.

Proceeding from this, the problem addressed by the invention is to make available an implant with which it is possible to treat prostates of different sizes.

A solution to this problem is described by the features of claim 1. Accordingly, provision is made that the length of the deployed implant is modifiable to a variable extent. Through the change of length of the stretched-out wire structure, the implant can be adapted individually to the patient anatomy and the outcome of treatment can thus be improved. Side effects, for example incontinence, can be avoided by the individual length adaptation. In order to adapt the length of the implant or of the wire structure in a targeted manner, the length of the enlarged prostate is measured prior to the treatment. This can be done, for example, by an imaging method, for example ultrasound, or some other method.

It is preferably provided, according to the invention, that a sleeve is able to be pushed over a proximal end region of the at least two wires of the wire structure, this sleeve at first being freely displaceable over the proximal end region of the wires. The at least two or three wires form the wire structure, which in turn forms the main constituent of the implant. At a distal end, the wires lie tightly together or touch and are connected to one another. The proximal ends of the wires are also connected to one another and, if appropriate, are connected to a holding means in order to be pushed through the catheter into the urethra and in order to pull the structure back out of the urethra after the treatment. Immediately after the initially folded wire structure is pushed out of the catheter, the wires, parallel in the folded state, expand into their predefined basket structure. This transition to the predefined basket shape is achieved through the shape-memory material used for the wires. After completion of the treatment, a slight axial tensile force is applied to the proximal end of the wires in order to transfer the wire structure back to the folded-up configuration. According to the invention, the sleeve is assigned to the proximal end region of the folded-up wires, which end region can measure a few millimeters to centimeters in length. The hollow-cylindrical sleeve encloses the two or three wires. Depending on the size of the prostate, measured in advance, the sleeve can be pushed to a defined position onto the wires.

Moreover, provision is made in particular that the sleeve is rigidly connectable to the at least two or three wires at the defined position, the rigid connection suppressing a relative movement between the wires and the sleeve. The sleeve prevents the wire structure from deploying to the predefined shape outside the catheter. In fact, it is only the region of the wires from the distal end as far as the sleeve that deploys, i.e. a shortened length. Accordingly, the further the sleeve is positioned in the distal direction onto the wires, the less the wires deploy and the less the implant has a disadvantageous effect on the proximal region near the external sphincter. The position of the holding element remains unaffected by this, such that the wires or the wire structure always protrude the same distance into the bladder, which is essential to the success of the therapy.

In a special exemplary embodiment of the invention, provision can in particular be made that the sleeve is a screw-type sleeve, a crimp sleeve, a click-fit sleeve, a latching sleeve or a sleeve having an inner passage whose diameter corresponds precisely to the sum of the diameters of the wires. In these embodiments of the sleeve, it is essential that the sleeve is able to fix itself to the wires in a simple manner, specifically in such a way that it maintains its position even in the event of slight mechanical tensile forces. The sleeve can be designed in one piece or as two or more parts.

It is conceivable in particular that the screw-type sleeve can be assembled from a first part and a second part, both parts having a hollow cylindrical design, and the wires being guided through the interior of this hollow cylinder. The first part has an inner thread and the second part has a sleeve with an outer thread, such that the two parts can be screwed together and the wires move through the two parts. A ring made of an elastic material is positioned between the two parts and, when the two parts are screwed together, expands and thus holds the wires for a rigid connection between the sleeve and the wires. The designs of the click-fit sleeve and of the latching sleeve are technically similar to the screw-type sleeve. The two aforementioned sleeve types also consist of two parts which can be connected to each other by application of a mechanical force, wherein an elastic ring between the two parts is deformed during the joining together and, in this way, a rigid connection is obtained between the sleeve and the wires. This connection between the two parts is reversible, such that the sleeve is removable or modifiable after the treatment but also during the treatment. It is for example conceivable that, by repositioning the sleeve during the treatment, the length of the implant is changed in order to react to the progress of the treatment. In this way, the treatment the person receives can be made even more efficient.

When using a crimp sleeve, the sleeve is fixed onto the wires using a crimping tool. The use of a crimp sleeve has the advantage that it is particularly resistant to axial forces which act on the connection between the sleeve and the wires. In a further alternative, provision is made that the internal diameter of the hollow cylindrical sleeve is tailored to the sum of the diameters of the wires, and the friction of the inner wall of the sleeve on the wires is sufficient to guarantee the fixing of the sleeve on the wires at a defined position.

In this case, greater force needs to be applied for the positioning of the sleeve in order to bring the sleeve into position on the wires counter to the frictional forces. In this exemplary embodiment, however, the sleeve is advantageously of very simple construction. In addition, the sleeve is able to be fastened without any great effort. Moreover, this kind of sleeve can be produced with a particularly small external diameter.

According to the invention, provision can be made that the sleeve is able to be fastened to the wires outside the person before the treatment or inside the person during the treatment. If the size of the prostate is already known before the treatment, the sleeve can be positioned and fastened in place outside the patient before the treatment, such that the implant, inside the urethra, opens with the predefined length. It is equally conceivable to determine during treatment where the sleeve is to be placed such that the prostate can be treated particularly efficiently. For this purpose, it is conceivable that further imaging instruments are introduced into the patient in order to determine the position. It is moreover conceivable that a further tool or a forceps is inserted into the patient in order to fix the sleeve onto the wires. In this embodiment, it is also conceivable for the position of the sleeve on the wires to be readjusted during the treatment, so as to be able to react efficiently during treatment to possible treatment outcomes.

According to the present invention, provision can be made that the external diameter of the sleeve is less than 3 mm. This diameter is largely dependent on the catheter used and/or on the implant used. If possible, it is likewise conceivable to use sleeves having a smaller external diameter, for example 2 mm or 1 mm.

In a further preferred exemplary embodiment of the invention, provision can be made that at least one of the wires, or a holding element of the implant, has markings, on the basis of which the length of the implant or the position of the sleeve is adjustable. Thus, it may be helpful to the operating surgeon if, for a given size of prostate, he simply has to push the sleeve as far as a defined marking, in order to fix the sleeve there to the wires. Depending on the position of the sleeve on the wires, the wire structure deploys with a defined length. The relationship between the size of the prostate and the marking can be taken, for example, from a previously created table.

A further solution to the problem stated at the outset is described by the features of claim 11. Accordingly, provision is made that the length of a holding element is modifiable to a variable extent. Here, the length of the wires remains unchanged, and only the length of the tongue-like holding element is changed. The clinical effect of this is the same as for the change of length of the wire structure. It is important here that the three wires protrude, as before, into the bladder. The tongue-like holding element in this exemplary embodiment is able to be varied and fixed in terms of its length by means of a sleeve of the kind described above. According to this exemplary embodiment, the position of the holding element in the urethra is adapted so that the implant can be optimally positioned, even for prostates of different sizes.

Alternatively, it is also conceivable that the holding element has a segment-like design and can be shortened at several predetermined breaking points. Depending on requirements and/or on the size of the prostate, individual distal elements of the holding element can be separated for the treatment. A sleeve, as in the previously described embodiment, is not needed.

A solution to the aforementioned problem is also described by the features of claim 14. Accordingly, provision is made that the wires and the tongue-like holding element are modifiable in terms of their lengths. The lengths of the wires and of the holding element can be varied as described above. By virtue of this targeted variation of the lengths of the wires and of the holding element, it is possible to react particularly efficiently and effectively to almost any patient anatomy and to any size of the prostate, and/or, depending on the anatomical circumstances, it is possible to choose between adapting the size of the wire structure or the length of the holding element. The sizes of the two aforementioned components can equally be adapted during treatment, as described above, such that the treatment of the patient leads to the best possible outcome.

A preferred exemplary embodiment of the present invention is explained in more detail below with reference to the drawing. In this drawing:

FIG. 1 illustrates a possible exemplary embodiment of an implant 10. It is expressly noted that this example is just one of many possible embodiments.

Figure 1:
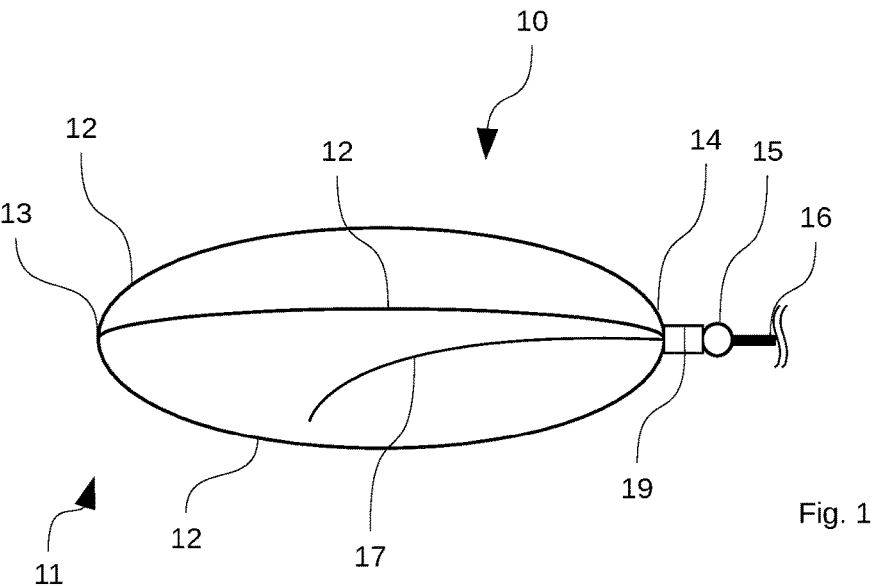
FIG. 1 shows a view of a deployed implant.

The exemplary embodiment of the implant 10 shown in FIG. 1 has a wire structure 11 with three wires 12. However, embodiments with two or four or more wires 12 are also conceivable. It has nonetheless been found that three wires 12 are particularly well suited for manipulating the tissue of the urethra. These wires 12 are advantageously wires made of stainless steel, a spring steel or a shape-memory material. Alternatively, it is also conceivable that the wires 12 are designed as plastic rods. Thus, in a particularly advantageous exemplary embodiment, provision is made that the plastic is biodegradable. The implant 10 thus at least partially breaks up after a certain time within the body, and therefore a further intervention for recovering the implant 10 is not needed.

The wires 12 are connected to one another at their distal ends 13. The opposite, proximal ends 14 of the wires 12 are brought together in a common connection body 15. This connection body 15 is shown as a ball in the figures, but it can also have any other shape. A holding means 16 is arranged proximally on the connection body 15. This holding means 16, which can be designed as a thread, as a flexible wire or as a pin, serves in particular for placing the implant 10 in the urethra and also for withdrawing the implant 10 from the urethra after treatment has been competed. Accordingly, the holding means 16 is guided out of the body during the treatment.

FIG. 1 also illustrates, highly schematically, a tongue-like holding element 17. After the implant 10 has been correctly positioned in the urethra, this holding element 17 engages in the tissue and serves for fixing the implant 10 in the region to be treated. This holding element 17 can preferably be made from the same material as the wires 12 and is likewise connected to the holding means 16. On account of the tongue-like shape of the holding element 17, the latter acts like an anchor for the implant 10. By pulling it back a short distance in the proximal direction after the positioning of the implant 10, the holding element 17 is fixed in the tissue.

In the exemplary embodiment in FIG. 1, the sleeve 19 according to the invention is also shown. This sleeve is a hollow cylinder which is pushed over the proximal ends 14 or over the proximal region of the wires 12. Initially, i.e. before the treatment, this sleeve 19 is freely displaceable over the wires 12. For setting a defined length of the implant 10 or of the wire structure 11, the sleeve 19 can be moved to and fro along the folded wires 12 and fixed at a suitable position. The distance between the distal end 13 and the sleeve 19 then defines the length of the stretched-out implant 10. In the exemplary embodiment shown in FIG. 1, the sleeve 19 is positioned directly in front of the connection body 15, i.e. the sleeve 19 encloses the proximal ends 14 of the wires 12. As a result of this positioning of the sleeve 19, the wire structure 11 stretches to its maximum length. The length of the implant 10 or of the wire structure 11 can be determined according to the size of the prostate. This size or length of the prostate is determined prior to the treatment, such that, even before the implant 10 is inserted into the body of the patient, the optimal length of the wire structure 11 is adjustable by displacement and fixing of the sleeve on the wires 12.

Figure 2:
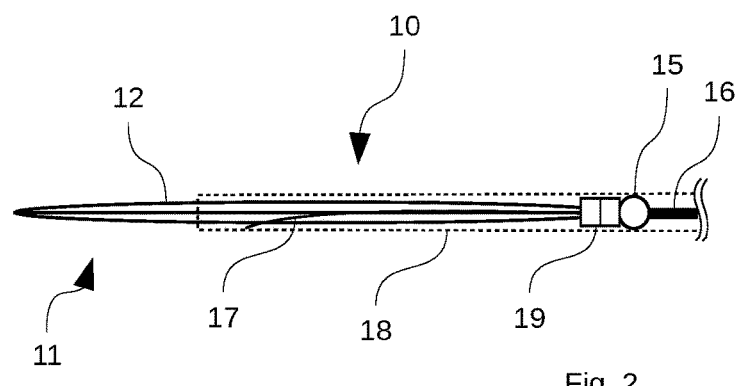
FIG. 2 shows a view of the implant in the folded-up state.

For the treatment of BPH syndrome, the implant 10 is first inserted in the folded state into the patient's urethra through a tubular catheter 18, as is shown schematically in FIG. 2. In the exemplary embodiment according to FIGS. 1 and 2, the sleeve 19 is situated at the proximal end 14 of the wires 12, such that the wire structure 11 has a maximum length. As soon as the catheter 18 has been brought to the correct position inside the urethra, the implant 10 is pushed out of the catheter 18 and, if appropriate, the catheter 18 is at the same time pulled in the proximal direction out of the urethra. As a result of the material that is chosen, the wires 12 outside the catheter 18 stretch out to form the wire structure 11 shown in FIG. 1, specifically as far as the sleeve 19. Alternatively, it is also conceivable that the wires 12 are stretched out to form the wire structure 11 by means of an axial pull on the holding means 16. If, during the stretching out of the wire structure 11, the implant 10 shifts away from the optimal position, it is possible to move the implant 10 back to the correct position.

Figure 3:
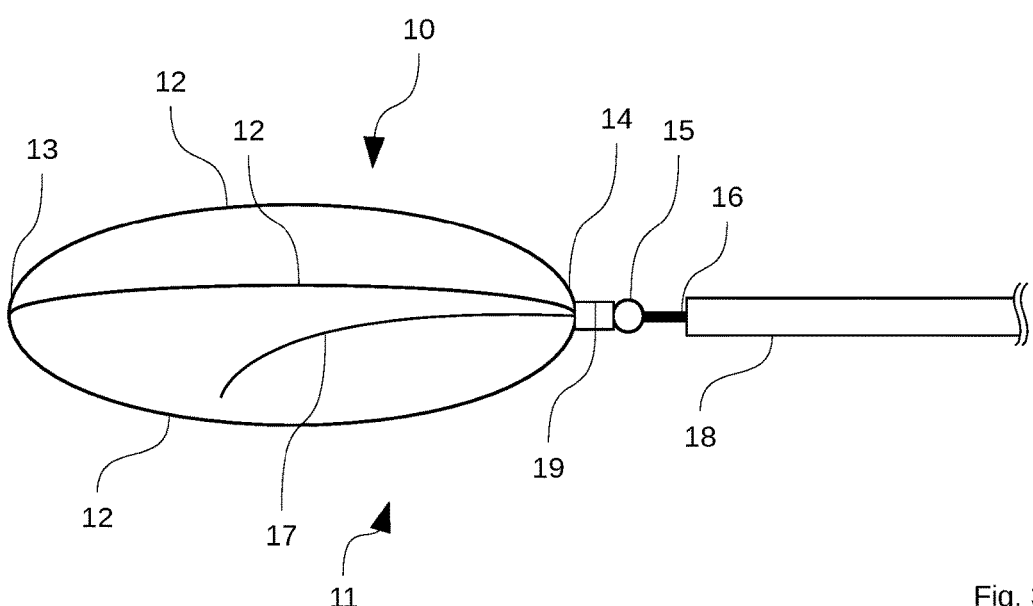
FIG. 3 shows a view of the implant in the deployed state.

As soon as the wire structure 11 has reached the optimal shape or the maximum expansion for treating the tissue and the holding element 17 has anchored itself in the tissue, the catheter 18 is pulled in the proximal direction out of the urethra. By virtue of the anchoring provided by the holding element 17, the implant 10 remains at the predetermined position, the holding means 16 being guided out of the urethra (FIG. 3). After the treatment has been completed, the catheter 18 is inserted again into the urethra via the holding means 16, and the stretched-out wire structure 11 is pulled back through the holding means 16 into the catheter 18, the wires 12 being pulled together on the circumference of the catheter 18. In the folded-together state, the implant 10 in the catheter 18 can be pulled back out of the urethra.

For treatment of a smaller prostate, the length of the implant 10 can be varied. It will be seen from FIG. 4 that the sleeve 19 has been displaced in the distal direction compared to the exemplary embodiment according to FIGS. 1 to 3. The sleeve 19 is not only displaced in the distal direction but also fixed at this position. This positioning of the sleeve 19 and its fixing take place outside the catheter 18 in accordance with the determined size of the prostate. Apart from the position of the sleeve 19 on the wires 12, no other changes have been made in relation to the exemplary embodiment according to FIGS. 1 to 3. As the implant 10 is guided out of the catheter 18, the wires 12 stretch out equally, as described above, but only as far as the sleeve 19. The sleeve 19 suppresses complete deployment of the implant 10. Thus, in the exemplary embodiment of FIG. 5, the implant 10 is accordingly shorter. This shortened length of the implant 10 is tailored to the size of the prostate that is to be treated. As a result of this adjustment of the length of the wire structure 11, no other tissues or muscles or the like are accidentally damaged during the treatment. Rather, this adjusted length ensures that pressure is applied to precisely the region that is to be treated.

Just like the length of the wires 12, the length of the tongue-like holding element 17 can also be varied. The holding element 17 can equally be guided through the sleeve 19. Exemplary embodiments are conceivable in which only the holding element 17 is guided through the sleeve 19 and the wires 12 in their stretched out state are not affected, or the wires 12 are guided together with the holding element 17 through the sleeve 19. If only the holding element 17 is guided through the sleeve 19 and shortened in length, it is not the length of the implant 10 that is changed but the position at which the implant 10 is fixed inside the bladder neck. The implant 10 can protrude into the bladder but will not come into contact with the external sphincter.

Figures 4, 5, 6:
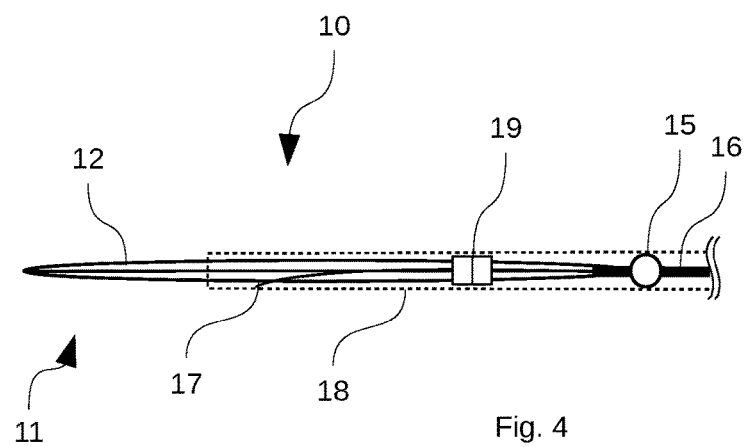
FIG. 4 shows a view of the implant in the shortened, folded-up state.
FIG. 5 shows a view of the implant in the shortened, deployed state.
FIG. 6 shows a sectional view of an exemplary embodiment of a sleeve.

To ensure that the implant 10 maintains its adapted length during the treatment, it is extremely important that the sleeve 19 is rigidly connectable to the wires 12 and/or the holding element 17. It is only through this rigid connection that the wires 12 stretch distally from the sleeve 19, specifically without the sleeve 19 being displaced in the proximal direction. For this fixing of the sleeve on the wires 12, different embodiments of the sleeve 19 are provided. FIG. 6 illustrates a possible exemplary embodiment. The sleeve 19 is composed of a first part 20 and a second part 21. These two parts 20, 21 are designed like hollow cylinders and can be screwed into one another. Moreover, the two parts 20, 21 have a passage 22 through which the wires 12, which are shown by way of example in the exemplary embodiment according to FIG. 6, and/or the holding element 17 can be guided. The first part 20 has an inner thread 23, which corresponds with an outer thread 24 of the second part 21. The outer thread 24 of the second part 21 is arranged on a region which has a reduced diameter and which can be screwed into the first part 20. Moreover, an elastic ring 25 is positioned between the first part 20 and the second part 21. When the first part 20 is screwed together with the second part 21, this elastic ring 25 is compressed, such that the free passage 22 is reduced. By this deformation of the ring 25, wires 12 inside the sleeve 19 are fixed, and therefore a relative movement between the wires 12 and the sleeve 19 is suppressed.

Provision is made that the sleeve 19 is screwed together outside the catheter 18 prior to the treatment. It is conceivable that markings are located on the wires 12 in order to give the operating surgeon an indication of where the sleeve is to be placed. With the aid of the markings, a defined length of the implant can be set. It is equally conceivable that the sleeve 19 is screwed together inside the catheter. For example, even after the implant 10 has been placed in the urethra, the screw connection can be opened during the treatment and, after the sleeve has been displaced on the wires 12, can be screwed together again, such that the length of the implant 10 can be actively changed during the treatment. For this purpose, it is conceivable that the sleeve 19 inside the urethra is gripped and actuated using a special tool.

In an alternative embodiment of the sleeve, provision can be made that it is designed as a click-fit or latching sleeve. In this case, two parts are not screwed together as described above with reference to FIG. 6, and instead they click or latch onto each other. In a further embodiment of the sleeve, provision can be made that it is designed as a crimp sleeve. The crimp sleeve is guided over the wires 12 outside the body, prior to the treatment, and pressed using a crimping tool. A crimp connection of this kind provides particularly reliable fixing of the sleeve and, in addition, is particularly favorable in terms of its production.

Independently of its design, the sleeve 19 can produced from a metal, plastic or a ceramic. The diameter of the sleeve 19, or of the two parts 20, 21, is largely dictated by the internal diameter of the catheter 18 but is generally less than 3 mm. Embodiments are conceivable in which the diameter of the sleeve can also be 1 mm to 2 mm.

LIST OF REFERENCE SIGNS

10 implant
11 wire structure
12 wire
13 distal end
14 proximal end
15 connection body
16 holding means
17 holding element
18 catheter
19 sleeve
20 first part
21 second part
22 passage
23 inner thread
24 outer thread
25 ring

The invention claimed is:

1. A removable implant for treating a urinary tract of a person by application of a local ischemic pressure to tissue of urinary organs comprising a wire structure with at least two wires, the implant in a folded state being insertable, with a distal end to the front, into a urethra and being deployed to provide the wire structure in the urethra in order to treat the tissue, wherein a length of the implant is modifiable to a variable extent, wherein the removable implant further comprises a sleeve configured to be pushed over a proximal end region of the at least two wires, the sleeve being freely displaceable over the proximal end region of the wires, and wherein when the length of the implant is shortened via displacement of the sleeve, the sleeve is entirely located between the proximal end region of the implant and a distal end of the implant, such that at least a portion of the wire structure is exposed at the proximal end region.

2. The removable implant as claimed in claim 1, wherein the sleeve is rigidly connectable to the at least two wires, a relative movement between the wires and the sleeve being suppressed by the rigid connection.

3. The removable implant as claimed in claim 1, wherein the sleeve is a screw-type sleeve, a crimp sleeve, a click-fit sleeve, a latching sleeve or a sleeve having an inner passage whose diameter corresponds precisely to the sum of the diameters of the wires.

4. The removable implant as claimed in claim 1, wherein the length of the implant is adjusted by the positioning of the sleeve on the at least two wires, the length of the deploying portion of the wires being set by the fixing of the sleeve on the wires.

5. The removable implant as claimed in claim 3, wherein the screw-type sleeve can be assembled from a first part and a second part, the first part having an inner thread and the second part having a sleeve with an outer thread, the second part being able to be screwed together with the first part, and an elastic ring being able to be clamped between the first part and the second part.

6. The removable implant as claimed in claim 1, wherein the sleeve is able to be fixed to the wires outside the person before a treatment or inside the person during the treatment.

7. The removable implant as claimed in claim 1, wherein the sleeve is able to be fastened releasably to the wires.

8. The removable implant as claimed in claim 1, wherein the sleeve has an external diameter of less than 3 mm.

9. The removable implant as claimed in claim 1, wherein at least one of the wires, or a holding element of the implant, has markings, on the basis of which the length of the implant or the position of the sleeve is adjustable.

10. A removable implant for treating a urinary tract of a person by application of a local ischemic pressure to tissue of urinary organs comprising a wire structure with at least two wires, the implant in a folded state being insertable, with a distal end to the front, into a urethra and being deployed to provide the wire structure in the urethra in order to treat the tissue, and having a holding element, by which the position of the implant inside the urinary tract is able to be fixed, wherein a length of the holding element is modifiable to a variable extent, wherein the removable implant further comprises a sleeve configured to be pushed over a proximal end region of the at least two wires, the sleeve being freely displaceable over the proximal end region of the wires, and wherein when the length of the implant is shortened via displacement of the sleeve, the sleeve is entirely located between the proximal end region of the implant and a distal end of the implant, such that at least a portion of the wire structure is exposed at the proximal end region.

11. The removable implant as claimed in claim 10, wherein a sleeve is able to be pushed over a proximal end region of the holding element.

12. The removable implant as claimed in claim 10, wherein the holding element has, at a distal end, predetermined breaking points, by which the length of the holding element can be changed in a targeted manner.

13. A removable implant for treating a urinary tract of a person by application of a local ischemic pressure to tissue of urinary organs comprising a wire structure with at least two wires, the implant in a folded state being insertable, with a distal end to the front, into a urethra and being deployed to provide the wire structure in the urethra in order to treat the tissue, and having a holding element, by which the position of the implant inside the urinary tract is able to be fixed, wherein, a length of the implant and the length of the holding element are modifiable to a variable extent, wherein the removable implant further comprises a sleeve configured to be pushed over a proximal end region of the at least two wires, the sleeve being freely displace-
able over the proximal end region of the wires, and
wherein when the length of the implant is shortened via
displacement of the sleeve, the sleeve is entirely
located between the proximal end region of the implant
and a distal end of the implant, such that at least a
portion of the wire structure is exposed at the proximal
end region.

14. The removable implant as claimed in claim 1, wherein
the sleeve is shorter in length than the wire structure.

* * * * *